United States Patent
Feiweier

(10) Patent No.: US 10,048,339 B2
(45) Date of Patent: Aug. 14, 2018

(54) METHOD AND MAGNETIC RESONANCE SCANNER FOR GENERATING A DATA SET

(71) Applicant: Siemens Aktiengesellschaft, Munich (DE)

(72) Inventor: Thorsten Feiweier, Poxdorf (DE)

(73) Assignee: Siemens Aktiengesellschaft, Munich (DE)

( * ) Notice: Subject to any disclaimer, the term of this patent is extended or adjusted under 35 U.S.C. 154(b) by 725 days.

(21) Appl. No.: 14/603,657

(22) Filed: Jan. 23, 2015

(65) Prior Publication Data

US 2016/0216350 A1 Jul. 28, 2016

(30) Foreign Application Priority Data

Jan. 23, 2014 (DE) ........................ 10 2014 201 205

(51) Int. Cl.
| | | |
|---|---|---|
| *G01V 3/00* | (2006.01) | |
| *G01R 33/48* | (2006.01) | |
| *A61B 5/055* | (2006.01) | |
| *G01R 33/56* | (2006.01) | |
| *G01R 33/565* | (2006.01) | |

(52) U.S. Cl.
CPC .......... *G01R 33/4828* (2013.01); *A61B 5/055* (2013.01); *G01R 33/565* (2013.01); *G01R 33/5607* (2013.01)

(58) Field of Classification Search
CPC .............. G01R 33/543; G01R 33/5659; G01R 33/3415; G01R 33/36; A61B 5/055
USPC ......................................................... 324/309
See application file for complete search history.

(56) References Cited

U.S. PATENT DOCUMENTS

| | | | | |
|---|---|---|---|---|
| 5,117,187 A | * | 5/1992 | Granot ............... | G01R 33/4835 324/309 |
| 6,064,203 A | * | 5/2000 | Bottomley ............. | G01R 33/50 324/307 |
| 6,850,793 B1 | * | 2/2005 | Miyazaki ............... | G01R 33/54 324/307 |
| 2004/0152969 A1 | * | 8/2004 | Zhang ................. | G01R 33/5611 600/422 |
| 2005/0194974 A1 | * | 9/2005 | Feiweier ............ | G01R 33/5659 324/309 |
| 2010/0259260 A1 | * | 10/2010 | Lee ....................... | G01R 33/446 324/309 |

(Continued)

OTHER PUBLICATIONS

Bydder et al., "MR Imaging: Clinical Use of the Inversion Recovery Sequence," Journal of Computer Assisted Tomography, vol. 9(4) (1985), pp. 659-675.

(Continued)

*Primary Examiner* — Walter L Lindsay, Jr.
*Assistant Examiner* — Frederick Wenderoth
(74) *Attorney, Agent, or Firm* — Schiff Hardin LLP

(57) ABSTRACT

In a method and a magnetic resonance scanner for generating a data set, a first RF pulse is applied simultaneously with a first gradient having a first amplitude and a first polarity, and at least one second gradient is applied having a second amplitude and a second polarity. A second RF pulse is applied simultaneously with a third gradient having a third amplitude and a third polarity. The third amplitude is different from the first amplitude and/or the third polarity is different from the first polarity. The scan signal generated using the second RF pulse is then read out.

16 Claims, 9 Drawing Sheets

(56) References Cited

U.S. PATENT DOCUMENTS

| | | | | |
|---|---|---|---|---|
| 2010/0264922 A1* | 10/2010 | Xu | .................. | A61B 5/055 324/309 |
| 2012/0025826 A1* | 2/2012 | Zhou | .................. | G01R 33/4833 324/309 |
| 2013/0088226 A1* | 4/2013 | Miyazaki | .......... | G01R 33/5607 324/309 |

OTHER PUBLICATIONS

Dixon, "Simple Proton Spectroscopic Imaging," Radiology, vol. 153 (1984), pp. 189-194.

Meyer et al., "Simultaneous Spatial and Spectral Selective Excitation," Magnetic Resonance in Medicine, vol. 15 (1990), pp. 287-304.

Haase et al., "1H NMR chemical shift selective (CHESS) imaging," Phys. Med. Biol., vol. 30, No. 4 (1985), pp. 341-344.

Ivanov et al., "A Simple Low-SAR Technique for Chemical-Shift Selection with High-Field Spin-Echo Imaging," Magnetic Resonance in Medicine, vol. 64 (2010), pp. 319-326.

Bottomley et al., "In vivo nuclear magnetic resonance chemical shift imaging by selective irradiation," Proc. Natl. Acad. Sci., vol. 81 (1984), pp. 6856-6860.

Thomasson et al., "Phase-Modulated Binomial RF Pulses for Fast Spectrally-Selective Musculoskeletal Imaging," Magnetic Resonance in Medicine, vol. 35 (1996), pp. 563-568.

Park et al., "Gradient Reversal Technique and Its Applications to Chemical-Shift-Related NMR Imaging," Magnetic Resonance in Medicine, vol. 4 (1987), pp. 526-536.

Nagy et al., "Efficient fat suppression by slice-selection gradient reversal in twice-refocused diffusion encoding," Magnetic Resonance in Medicine, vol. 60 (2008), pp. 1256-1260.

Ribeiro et al., "STIR, SPIR and SPAIR techniques in magnetic resonance of the breast: A comparative study," J. Biomedical Science and Engineering, vol. 6 (2013), pp. 395-402.

Lauenstein et al., "Evaluation of Optimized Inversion-Recovery Fat-Suppression Techniques for T2-Weighted Abdominal MR Imaging," Journal of Magnetic Resonance Imaging, vol. 27 (2008), pp. 1448-1454.

\* cited by examiner

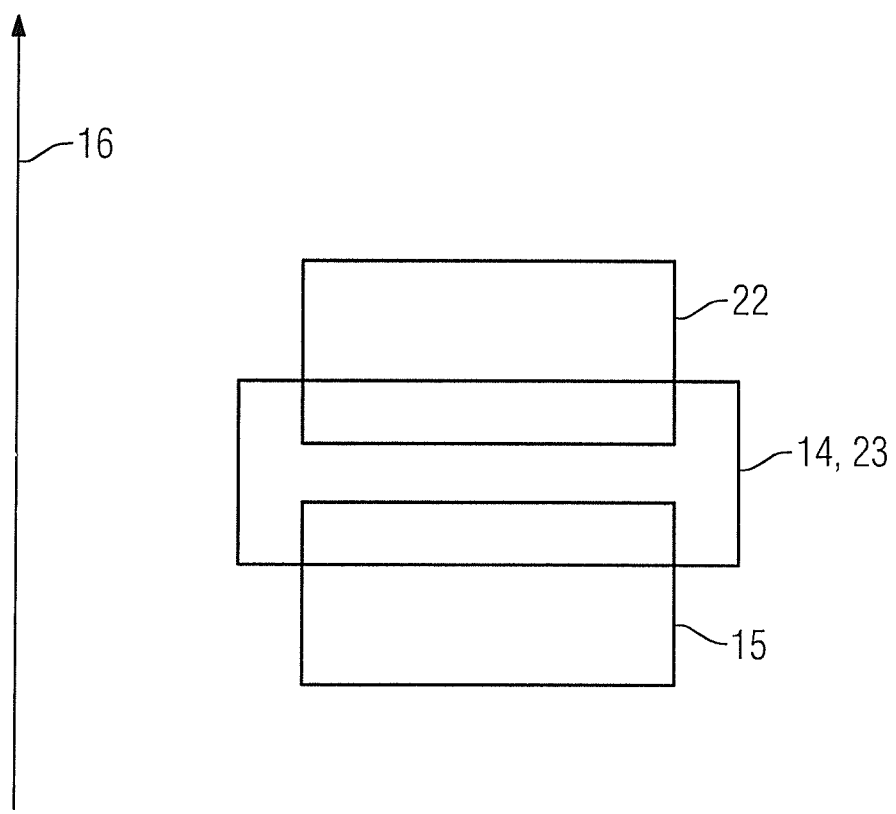

METHOD AND MAGNETIC RESONANCE SCANNER FOR GENERATING A DATA SET

BACKGROUND OF THE INVENTION

Field of the Invention

The present invention relates to a method and a magnetic resonance scanner for generating a data set.

Description of the Prior Art

For magnetic resonance examinations, examination objects are placed in a magnetic field in order to produce, in the examination object, a longitudinal magnetization of nuclei spins in the direction of the external magnetic field, which magnetization can be used for magnetic resonance experiments. Different nuclei can be examined, e.g. hydrogen nuclei (protons), sodium nuclei, carbon nuclei and some others.

The resonant frequencies of the examinable nuclei are different. At a magnetic field strength of 1.5 T, protons have a resonant frequency of approximately 63 MHz, sodium nuclei a resonant frequency of 16 MHz. A differentiation in the resonant frequencies, particularly in the proton resonant frequencies, is additionally caused by the nuclei being in different chemical environments. This frequency shift is also termed "chemical shift". Without the chemical shift, a magnetic resonance spectrum would have only little diagnostic value. As a result of the chemical shift, the resonant frequencies of the protons of fat and water have a separation, the separation of the dominant fat resonance being about 225 Hz or field-independently about 3.3 ppm at 1.5 T.

However, in magnetic resonance imaging this effect results in "chemical shift artifacts". For better understanding, the chemical environment is regarded in simplified terms as an additional magnetic field that shifts the resonant frequency. This causes two problems. The spatial encoding has superimposed thereon the read gradient of an additional magnetic field, so viewed as a whole the magnetic field for water protons and fat protons remains different. The additional magnetic field is also once again dependent on the fat in which the protons are bound. However, the differences are less, for which reason a distinction is only made between fat and water in the following description.

For data acquisition with simultaneous switching of a readout gradient, in the image produced from the scan data this resonance shift between water and fat causes the fat signal or fat image to be shifted compared to the water signal or water image.

In addition, for slice selection during which a gradient is switched simultaneously with an RF excitation pulse, this shifting of the resonances causes the slices from which water protons and fat protons are selected to be shifted relative to one another.

A gradient is a non-constant magnetic field which is superimposed on the main magnetic field B0. A gradient is used to make the resonant frequency of the protons spatially dependent.

In the following, the signals or also the protons of water are also termed water signal, water component or water component signal. Fat is similarly designated. Fat suppression means the suppression of the fat component signal.

In order to prevent the chemical shift artifact, it is known to suppress the fat signals. Several methods for achieving fat suppression are known:

One means of fat suppression is spectrally selective suppression. From Bottomley et al., In vivo nuclear magnetic resonance chemical shift imaging by selective irradiation, Proc. Natl. Acad. Sci. USA, Vol. 81, pp. 6856-6860, 1984 it is known to first selectively excite the fat protons using an amplitude-modulated radiofrequency pulse. For this purpose, a gradient must not be switched while the RF pulse is applied. This RF pulse is therefore not slice selective, but only frequency selective. This causes the excited protons to be folded over in the transverse plane. Slice selection is not achieved until a subsequent spin echo sequence in which a slice selective excitation pulse is followed by a refocusing pulse. The disadvantage of this method is that, if the 90° or 180° pulses are sub-optimal, a residual signal of the unwanted component will remain.

A variant is described in Haase et al., 1H NMR chemical shift selective (CHESS) imaging, Phys. Med. Biol., 30(4), pp. 341-344, 1985. After the first, frequency selective 90° excitation pulse, a spoiler gradient is applied that dephases the signal of the fat component that was folded over in the transverse plane by the first RF pulse. How well the subsequent RF pulses are adjusted is therefore immaterial.

For spectrally selective fat suppression, the unwanted component is therefore first excited by a frequency selective 90° RF pulse such that it has no effect on the subsequent experiment. However, slice selection is not possible until thereafter, as no slice selection gradient can be applied during injection of a frequency selective RF pulse.

Another form of fat suppression is that of the inversion methods. These constitute a special case of the inversion recovery (IR) sequences in which the magnetization is initially excited using a 180° pulse, also known as the inversion pulse.

Representative of this type of fat suppression method is the so-called STIR (short TI inversion recovery) sequence, see Bydder and Young, MR Imaging: Clinical Use of the Inversion Recovery Sequence, J Comp Assist Tomogr, 9(4), pp. 659-675, 1985. Here an inversion pulse is injected which folds all the components, i.e. water and fat protons, through 180°. A waiting time which is selected such that the relaxation curve of the fat component passes through the zero crossing is then allowed to elapse. At this point in time the excitation pulse of a spin echo sequence is injected, wherein only the water protons provide a signal contribution, as their signal has no zero crossing. It is considered a disadvantage of this method that the signal of the water protons is also comparatively small at the zero crossing time of the other component. Also the waiting time is relatively long, which means that overall exposure time is increased.

The SPAIR (spectral attenuated inversion recovery) method is also known. In contrast to STIR, the 180° inversion pulse is selectively targeted at the fat protons, which means that the water component signal is not reduced at the zero crossing of the fat. However, the long exposure time remains. An application of this method is described in Lauenstein et al., Evaluation of Optimized Inversion-Recovery Fat-Suppression Techniques for T2-Weighted Abdominal MR Imaging, JMRI, 27(6), pp. 1448-1454, 2008.

A variant of the SPAIR sequence is the SPIR (spectral presaturation with inversion recovery) method. In contrast to SPAIR, the first RF pulse is not a 180° inversion pulse, but a 100° to 110° pulse. This enables the exposure time to be reduced, as the zero crossing of the fat signal is reached more quickly.

An overview study of the fat inversion methods is provided by Ribeiro et al., STIR, SPIR and SPAIR techniques in magnetic resonance of the breast: A comparative study, J. Biomedical Science and Engineering, 6, pp. 395-402, 2013.

Another way of utilizing the different resonant frequencies of the water and fat protons is employed in the Dixon technique named after its inventor, cf. Dixon W. T., Simple Proton Spectroscopic Imaging, Radiology, 153 (1), pp. 189-194, 1984. Here two images are acquired using different echo times, wherein the echo times are selected such that the signal contributions of fat and water add to a maximum in one instance and cancel each other out to a minimum in the next image. These images can be set against one another so as to produce pure water and fat images. However, two images always have to be acquired and prior knowledge concerning the echo time settings is also required.

A procedure differing from the techniques described is constituted by SSGR (slice selective gradient reversal), see Park H W et al., Gradient Reversal Technique and its Applications to Chemical-Shift Related NMR Imaging, Magn. Res. Med., 4, pp. 526-536, 1987. This makes use of the fact that, as described in the introduction, the different resonant frequencies also shift the slices of the fat component and water component relative to one another. In a spin echo sequence having two slice selective RF pulses whose center frequency is tuned to the water frequency, the polarity of the gradient of the refocusing pulse is reversed compared to the polarity of the gradient of the excitation pulse, causing the fat signal to be rephased only partially or not at all and the slice selection gradient to additionally have a dephasing effect on the fat protons. The two RF pulses are not chemically selective.

In order to achieve accelerated image acquisition, the thus obtained spin echo can also be read out using EPI (echo planar imaging), cf. Ivanov D. et al., A Simple Low-SAR Technique for Chemical-Shift Selection with High-Field Spin-Echo Imaging, Magn. Res. Med., 64, pp. 319-326, 2010.

It is also known to use the SSGR method with two refocusing pulses, see Nagy Z. and Weiskopf N., Efficient Fat Suppression by Slice-Selection Gradient Reversal in Twice-Refocused Diffusion Encoding, Magn. Res. Med., 60, pp. 1256-1260, 2008. This is a variant of SE-EPI using two refocusing pulses for diffusion weighting.

The techniques based on gradient reversal (SSGR) always require at least one 180° refocusing pulse.

SUMMARY OF THE INVENTION

An object of the present invention is to provide a magnetic resonance scanner and a method that permit improved acquisition of data sets with suppression of unwanted components.

In the following, the terms wanted and unwanted component are used instead of water and fat component, as the method according to the invention is suitable for suppressing both the water signal and fat signal or signal of another chemically shifted proton spin species such as silicon protons, or even one of two components of another nucleus as protons. When reference is made to fat suppression in examples described, this only constitutes a preferred embodiment.

According to the invention, a first slice selective RF pulse is injected while a first gradient having a first amplitude and a first polarity is simultaneously applied. This is a normal procedure for exciting slice selective magnetization or for refocusing. RF is a commonly used designation for a frequency extending at least from approximately 20 MHz for magnetic fields of 0.5 T to 900 MHz for magnetic fields of approximately 21 T in the case of protons. More generally, RF is any frequency at which magnetic resonance experiments can be performed.

The desired slice thickness is achieved here by first defining an RF pulse having a particular pulse shape. Gauss-ian, sinc and other pulse shapes are known, the selection being made on the basis of, among other things, the type of application, e.g. excitation, inversion or refocusing pulse, SAR and homogeneity criteria, as the pulse shape also defines the shape of the slice and the energy to be applied for a particular excitation flip angle. Then the gradient strength of the slice gradient, often also called the slice gradient, is determined by multiplying a known conversion factor for the respective RF pulse by the desired slice thickness. For an RF pulse having a particular pulse shape, a minimum slice thickness therefore exists, namely that for which a gradient strength of 100%, i.e. the maximum gradient amplitude, is produced using the conversion factor. Smaller slice thicknesses can only be achieved using an RF pulse having a better shape in this respect.

If a gradient, in particular a slice gradient, is switched, a gradient is said to be applied. Staying with the slice gradient example, this means that, in the slice direction, a spatially dependent magnetic field is superimposed on the main magnetic fields B0 such that the resonant frequency of the spins constantly changes in the slice direction. The terms applying and switching denote two differently designed processes: Without an RF pulse being applied, the entire process is meant, i.e. the ramp-up of the gradient, the period at the desired strength and the ramp-down. In other words, the start and end ramp are included. If an RF pulse and a gradient are applied simultaneously, the gradient ramps lie outside the time during which the RF pulse is applied. In this time period, the gradient is at the selected strength. The gradient amplitude is normally constant while the RF pulse is applied, but it is also known to reduce the SAR using an adjustable combination of modulated amplitude and matched RF pulse shape, as is known from the VERSE method. While in the following the description is geared to the normal procedure, i.e. a constant gradient, this does not exclude alternatives to the slice selection described, these being expressly included. Should it also be necessary or advantageous for a particular RF pulse to use the ramps during the time of the RF pulse, this is likewise included. The average person skilled in the art will know how to apply an RF pulse and a gradient simultaneously so that a slice can be excited.

The slice direction can be set independently of the equipment coordinates and freely in space. For the method according to the invention it is not necessary for other gradient fields to be present or switchable in the read direction or phase encoding direction.

In short, a first gradient is therefore applied simultaneously with the first RF pulse. Its amplitude and polarity determine the thickness of the slice and its orientation. This gradient is normally a slice gradient, as it is applied simultaneously with an RF pulse. The first RF pulse is not an inversion pulse, but an excitation pulse.

The first gradient ends shortly after the end of the first RF pulse. The gradient remains at the desired strength while the RF pulse is applied and is not nulled out until the end of the RF pulse, which requires a short time of several dozen microseconds or a few milliseconds depending on the equipment.

Thereafter at least one second gradient is applied. Preferably three second gradients are applied, one in the slice direction, one in the read direction, and one in the phase encoding direction. This does not mean that an imaging experiment would have to be performed, as no gradient of any kind or phase encoding gradient are switchable in the read direction. Nor does a phase encoding gradient need to be switched in the phase direction. In this case these are pure direction instructions. If a number of second gradients are applied, these need have neither the same time duration nor the same strength. However, at least the same durations are normally used.

The second gradient or gradients cause the spins excited by the first RF pulse, i.e. the excited magnetization, to be dephased.

Therefore, an alternative formulation is that at least one second dephasing gradient or spoiler gradient or crusher gradient is applied.

Since, as described in the introduction, the water proton slice and fat proton slice are at least partially shifted relative to one another, the signal in respect of fat and water is eliminated in different slices.

After the second gradient, a second RF pulse is therefore applied simultaneously with a third gradient having a third amplitude and a third polarity, wherein the third amplitude is different from the first aptitude and/or the third polarity is different from the first polarity. The second RF pulse preferably has a flip angle that is not equal to 180°. The change in polarity and/or amplitude causes magnetization to be excited which originates at least partly from another spatial region than the magnetization that was excited by the first RF pulse. Because of the second gradient, this magnetization is at least partially saturated, on account of which the signal contribution from the newly excited region is dominant. The slice of the to-be-acquired or wanted component is therefore at least partially shifted in the case of the second RF pulse, whereas the slice of the unwanted component remains essentially the same.

Because of the change in the amplitude and/or polarity of the third gradient, this newly excited region essentially contains the signal contribution of a single component which is therefore dominant or exclusively present in the scan signal or rather data set.

Compared to SSGR, the position of the wanted component does not therefore remain the same, as no refocusing takes place using a 180° pulse.

The scan signal produced by the second RF pulse is finally read out. Any imaging or spectroscopic method can be used for this purpose. This will be described in detail later below.

Depending on how the signal is read out, it may be necessary to repeat individual steps or a plurality of the steps mentioned in order to generate a data set. Using a single readout, only spectroscopic datasets can be obtained, for imaging experiments a plurality of k-space lines is acquired in order to enable an image to be processed. A data set is therefore a set of data from which an image, a spectroscopic image or a spectrum can be obtained. Reconstruction methods such as GRAPPA can obviously be used here, a data set for producing an image does not therefore need to have the same number of k-space lines as the image subsequently has image lines.

As an alternative to changing the polarity, the gradient amplitude of the third gradient can also be varied. Here the pulse bandwidth of the second RF pulse is likewise preferably modified. By suitably selecting the pulse bandwidth, the slice thickness particularly of the fat slice can be maintained constant.

In addition or alternatively, the deflection direction of the second RF pulse can be changed compared to the first RF pulse. In particular, the sign of the deflection angle can be changed. For example, if a 90° x-pulse is used as the first RF pulse, the second RF pulse is a −90° x-pulse. Also the pulse duration can be adjusted to adjust the slice thickness.

The method is advantageously used for an examination object containing fat protons and water protons and the first and the third gradient are selected as a function of the first and second RF pulse such that the respective slices of the fat protons at least partially overlap in the longitudinal direction, i.e. in the direction of the slice normal. The method according to the invention can basically be used for all nuclei having a nuclear resonance. However, the method is preferably applied to protons, i.e. hydrogen nuclei. The proton signal has, as repeatedly described, at least two components, namely the water component and the fat component, wherein the protons contributing to the component signal are accordingly called water protons and fat protons. In addition, the method according to the invention can also be used to eliminate the signal of the water component. For this purpose it is merely necessary to modify the settings of the RF pulses and of the gradients such that the water component slice remains unchanged. However the signal of the fat protons is preferably reduced or suppressed.

The first and the third gradient are preferably selected as a function of the first and second RF pulse such that the respective slices of the fat protons have an identical thickness and/or an identical position in the longitudinal direction. The slice position is determined, as described, as a function of the resonant frequency of the protons, i.e. depending on the parameters of the RF pulse. On the other hand, the thickness of a slice is determined by the gradient strength. The gradient strength for a required slice thickness in turn depends on the pulse profile of the RF pulse. Purely for the sake of completeness, reference is made to the relation $$T=(2\pi/\gamma)*(B/G)$$

where, as known, the slice thickness T is determined by the bandwidth of the RF pulse B and the gradient amplitude G. The average person skilled in the art will be familiar with this, for which reason it is completely adequate at this juncture to predefine the object to be achieved.

The first RF pulse can preferably have a first center frequency and the second RF pulse a second center frequency that are different from one another. The purpose of the excitations by the first and the second RF pulse is that the selected or rather excited slice of the unwanted component, in particular of the fat component, is the same for both RF pulses, whereas the slice positions of the wanted component, in particular of the water component, are different. This can be achieved by, among other things, changing the center frequency of the RF pulses. For example, for fat suppression the resonant frequency of the water component in the slice to be excited is used as the center frequency of the first RF pulse or of the second RF pulse, whereas in the case of the respective other RF pulse a center frequency differing therefrom is selected. Changing the center frequency shifts the slice position of the excited water protons to the same extent as the center frequency changes. On the other hand, changing the amplitude and/or polarity from the first to the second gradient causes the slice of the excited fat protons to be kept at the same position.

Alternatively, the center frequency of the first RF pulse and the center frequency of the second RF pulse can possess a resonant frequency which does not correspond to the resonant frequency of the water protons, or more generally of the wanted component, in the slice to be excited. In particular, the center frequency of the first RF pulse and the center frequency of the second RF pulse can correspond to the resonant frequency of fat protons. The advantage of this alternative is that, apart from the polarity, the other settings of the third gradient can correspond to those of the first gradient, and therefore without further measures the fat protons automatically no longer provide a signal contribution.

The center frequency is here the center of the frequency band of an RF pulse.

It should be pointed out at this point that when carrying out the method according to the invention the signal of the unwanted component, in particular the fat signal, does not need to be completely eliminated. It can also be provided that small signal components selectively remain in the scan signal and therefore in the image or spectroscopy image or also spectrum computed therefrom in order to serve as orientation.

The first RF pulse can advantageously have a flip angle of 90°. With this setting the fat signal is completely suppressed. Alternatively, the first RF pulse can have a flip angle of less than 90°. A protein signal residue then remains in the scan signal.

The second RF pulse preferably has a flip angle of 90°. Alternatively, the second RF pulse can have a flip angle of less than 90°. This depends on how the magnetization is proceeded with. The first RF pulse and the first and the second gradient can be regarded as a preparation module which saturates the signal or rather the signal components at a specific slice position in each case. The second RF pulse can also be regarded as an excitation pulse of a scan sequence. A scan sequence or also pulse sequence is a particular sequence of RF pulses, gradients and waiting times for generating a data set. Known imaging scan sequences are e.g. a spin echo, gradient echo, FLASH, EPI, TrueFISP, etc. The majority of scan sequences can also be used to acquire a spectroscopy data set if the gradients for imaging are omitted. As explained above, for the method according to the invention it is merely necessary that gradients are used for slice selection.

If the signal is read out directly after the second RF pulse, a slice selective or slice related spectrum is obtained. However, the signal excited by the second RF pulse is preferably read out with an imaging experiment or an imaging scan sequence.

Accordingly, after the second gradient a scan sequence can be used to generate a data set, wherein the second RF pulse is the excitation pulse of the scan sequence. In particular, after the second gradient a FLASH, EPI or TrueFISP sequence can be used to generate the data set, wherein the second RF pulse is the excitation pulse of the respective scan sequence. In the case of a FLASH sequence, the second RF pulse usually has a flip angle of 5° to 30° and is injected as many times as the number of phase encoding steps provided. Obviously the scan sequences can also be acquired in a segmented manner, i.e. not all the phase encoding steps or rather k-space lines are acquired after the second gradient, but only a portion. For example, an experiment comprising 128 phase encoding steps is carried out. A possible segmentation consists of subdivision into 8 part-experiments, wherein 16 phase encoding steps are acquired for each part-experiment. The preparation module composed of the first RF pulse and the first and second gradient is then executed prior to each part-experiment, i.e. 8 times in the example, whereas the second RF pulse with the third gradient is used 16 times in each part-experiment 16, i.e. 128 times in all.

Instead of an imaging sequence, a slice selective spectroscopy sequence can be used after the second gradient to generate a data set, wherein the second RF pulse is the excitation pulse of the spectroscopy sequence. In contrast to the previous embodiment, there are no phase encoding steps, but obviously averagings, i.e. repetitions of the complete scan sequence, can also take place as in the case of the imaging sequences. In another embodiment, a slice selective and imaging spectroscopy sequence for generating a data set can be used after the second gradient, wherein the second RF pulse is the excitation pulse of the imaging spectroscopy sequence. This imaging method is known as "CSI" (chemical shift imaging). There are several types, including acquisition weighted CSI (AW-CSI) or density weighted CSI (DW-CSI). In the nucleus, the spatial encoding for imaging is performed by means of phase gradients only and without read gradients.

In the case of a segmented acquisition scheme, the central k-space data can advantageously be acquired first. The k-space data can be k-space lines or k-space points. This improves fat suppression, as the fat magnetization can relax during acquisition of the segments and therefore provides a signal contribution. As the central k-space data provides a low-frequency signal contribution, it is the main determining factor for the signal intensities. The segmentation of a scan sequence is generally known, as described above.

With particular advantage, all the method steps up to and including application of the second RF pulse and third gradient can be regarded as a preparation module. As a result of the preparation, the magnetization of the wanted component, in particular of the water protons, lies in the transverse plane. A refocusing pulse for producing a spin echo or a plurality of refocusing pulses for producing a multi-spin echo or turbo spin echo can also follow. These refocusing pulses can be slice selective. As described above, these can be imaging scan sequences or slice selective spectroscopy sequences or slice selective CSI sequences. Simultaneously with the refocusing pulses, gradients can be advantageously applied whose amplitude and polarity are selected such that the water protons excited by the second RF pulse are refocused, wherein in the case of one or more refocusing pulses the amplitudes and/or polarities change. This is a combination of the method according to the invention with the known SSGR.

An adiabatic RF pulse is preferably be used as the first RF pulse. Above a threshold value, adiabatic pulses have a constant flip angle, thereby reducing the B1 dependency.

Instead of or in addition to segmentation, the method according to the invention can be used to acquire at least two slices. Preferably at least three slices are acquired. In this context two or three slices of the wanted component, i.e. of the water protons, are obviously meant. Preferably, adjacent slices are not acquired directly one after another here, in order to prevent crosstalk. In an alternative embodiment, adjacent slices are consecutively acquired, wherein the saturation slice of the water protons is placed such that it lies in already acquired slices.

The object underlying the present invention is also achieved using a preparation module for magnetization preparation. This is characterized by the following:

a first RF pulse having a center frequency that is offset with respect to the resonant frequency of the nucleus under examination, in particular with respect to the resonant frequency of the main component of the nucleus under examination, and a first gradient having a first amplitude and a first polarity, wherein the polarity is negative, and wherein the gradient is applied simultaneously with the RF pulse, at least one second gradient which is applied after the first gradient.

The main component is the component having the information relevant to an examination. It mainly dominates the signal, but this is not obligatory. Automatic calibration, i.e. setting of the scanning parameters, is performed on this component, in particular the water component.

A negative polarity is present if negative numerical values are entered in the value table for the gradient. The value for a slice selection gradient is normally given positively, a negative value therefore representing a negative polarity and therefore a different polarity from that normally used for slice selection gradients.

The object of the present invention is also achieved by a magnetic resonance scanner. This has at least one gradient coil for producing a gradient field, an RF coil for generating RF pulses, and a control device. The magnetic resonance scanner is characterized in that the control device is designed to carry out the method as claimed in one of the preceding claims.

The above mentioned method can be implemented in the control device as software or alternatively as (hardwired) hardware.

The magnetic field of the magnetic resonance scanner advantageously has a field strength of at least 3 T. With increasing field strength, the "chemical shift" also increases, which means that higher gradient amplitudes can be used. As a result, field inhomogeneities have less effect.

Further advantageous embodiments of the method according to the invention correspond to the corresponding embodiments of the magnetic resonance scanner according to the invention.

BRIEF DESCRIPTION OF THE DRAWINGS

FIG. 15 shows a slice position for a single slice experiment in a second embodiment.

DESCRIPTION OF THE PREFERRED EMBODIMENTS

Figure 1:
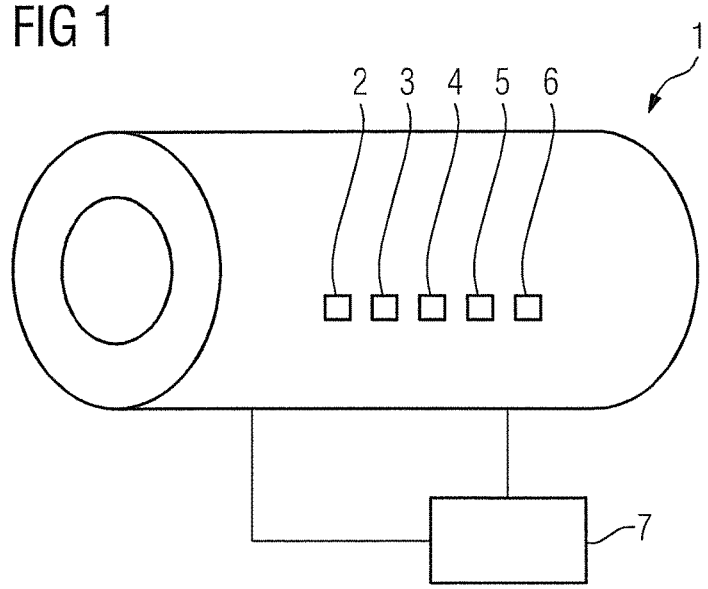
FIG. 1 shows a magnetic resonance scanner.

FIG. 1 shows a magnetic resonance scanner 1 having three gradient coils 2, 3 and 4, two RF coils 5 and 6 and a control device 7. Other components of the magnetic resonance scanner 1 such as the patient table are not shown for clarity. The RF coil 5 is implemented as an excitation coil and the RF coil 6 as a detection coil. The RF coil 6 is normally adapted to specific sections of the patient, e.g. as a "head coil", "chest coil" or "knee coil". The RF coil 5 is also known as a "body coil" and is less sensitive than the RF coil 6, but homogeneous over a larger area. This distribution of the RF coils is normal for magnetic resonance scanners 1 in the medical field, but not for equipment having bores measuring from a few to approximately 30 centimeters, where often the same RF coil is used for excitation and detection. Whether the excitation coil doubles as a detection coil is therefore immaterial and more or less equipment-dependent.

The gradient coils 2, 3 and 4 produce gradient fields in mutually orthogonal directions. In order to produce a resulting gradient in a predefined direction, the slice direction, read direction or phase encoding direction, the gradient fields of two gradient coils of all three gradient coils 2, 3 and 4 can also be superimposed. A gradient is therefore identical to the gradient field of a single gradient coil only in exceptional cases, and is usually a superposition of a number of gradient fields.

The method described is realized in software in the control device 7. In particular, after positioning of the patient, it can be carried out in an automated manner by determining the resonant frequencies of the water and fat component and establishing the other parameters as a function thereof.

Figure 2:
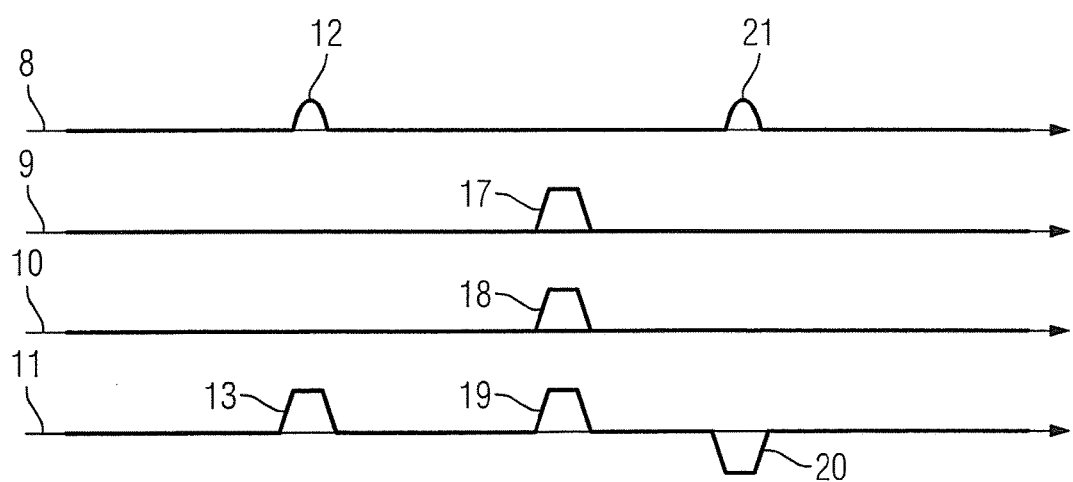
FIG. 2 shows a sequence diagram in a first embodiment of the invention.

FIG. 2 shows a section of the method described. It is represented in a form normally used in nuclear spin tomography, namely in the form of a sequence diagram. Here, and also in the following sequence diagrams, the axes 8, 9, 10 and 11 stand for a chronological sequence, the axis 8 for the radiofrequency pulses, also referred to as RF pulses, and the scan signal, the axis 9 for the read direction, the axis 10 for the phase direction, and the axis 11 for the slice direction. Not only with respect to the axes but also generally, the same reference characters are retained for identical items without this being explicitly stated in each figure.

To begin with, the first RF pulse 12 and the first gradient 13 are applied. The gradient 13 is therefore a slice gradient. The gradient 13 is also termed a slice selection gradient or slice-select gradient. The critical factor is that it is applied during injection of the RF pulse 12.

The RF pulse 12 excites the spins in a frequency-dependent manner but not in a chemically selective manner. If an examination object having hydrogen nuclei, i.e. protons, is scanned, the frequency dependency means that only one slice of the protons is excited in the examination object.

If the examined nucleus has two components having differing resonant frequencies, their excited slices are shifted with respect to one another. In the case of protons, the components fat and water are present whose resonant frequencies exhibit a difference of approximately 3.3 ppm. This difference is dependent on the strength of the main magnetic field B0 and is approximately 225 Hz at 1.5 T. Also to be found within the fat component are other differentiable resonance peaks which, however, have only small separations in the resonant frequency. These are negligible in the context of the method described, i.e. all the peaks of the fat component are regarded as one resonance.

The protons of the water component are also referred to as water protons and the protons of the fat component as fat protons. The method described is basically not limited to water and fat and fat suppression, rather it can be used for any nucleus whose resonant signal has two or more components. However, fat suppression is a preferred embodiment. In the case of protons, for example, the signal of silicon protons could also be suppressed.

Figure 3:
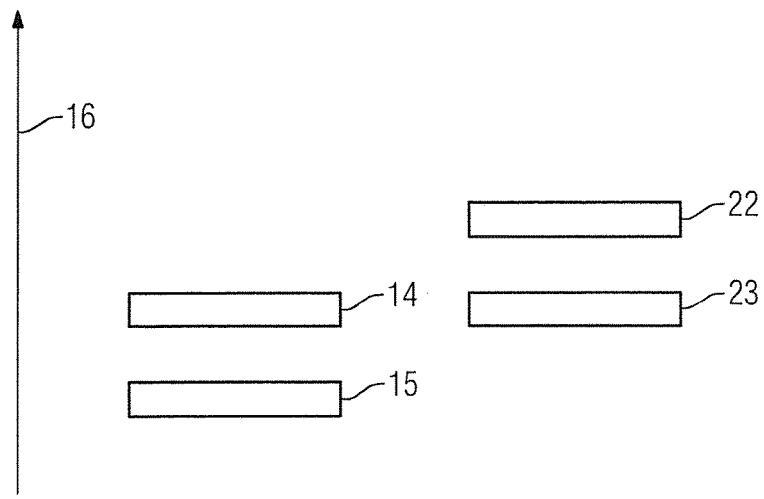
FIG. 3 shows a slice position for a single slice experiment of the invention.

The slices excited by the RF pulse 12 are shown in FIG. 3. The slice 15 is the slice of the water component, the slice 14 the slice of the fat component. Whether the slices 14 and 15 overlap depends on a number of constraints. The minimum thickness of the slices 14 and 15 depends on the maximum applicable gradient strength of the gradient 13 and the bandwidth of the RF pulse. The former also depends on the power of the gradient coils 2, 3 and 4. The distance between the slice centers increases with increasing B0 field strength, i.e. is greater for high field equipment than for low field equipment. From this information it can be determined whether or not the slices are completely separable.

Here the axis 16 represents the longitudinal direction to which the slices 14 and 15 are perpendicular.

Whether the water or fat slice is on top or below depends on the polarity of the gradient. The method according to the invention is not limited to the water slice initially being "below", this being purely by way of example.

The method will be described in further detail with reference to FIG. 2. The RF pulse 12 and the gradient 13 are followed by the gradients 17, 18 and 19. These dephase the magnetization of the slices 14 and 15, as a result of which the signal is saturated in these slices and must first relax again before there is a signal.

At this point some general comments shall be made about time variables: the more time there is between the first RF pulse 12 and the second RF pulse 21, the more fat signal is relaxed again. Nevertheless, there are mostly insignificant waiting times between successive elements such as a gradient and a subsequent RF pulse. Like all times, these cannot be specified in a generally valid manner, as they are greatly equipment-dependent and minimum waiting times can easily differ by a factor of 10, for example. However, the times can be inferred from the meaning and purpose of the sequence described and can therefore be selected according to the equipment by the average person skilled in the art There are two possibilities for achieving fat suppression by reversing the polarity of the slice gradient:

The polarity of the slice gradient can simply be reversed and it can be applied simultaneously with the RF pulse 21 as gradient 20. The center frequency is then preferably placed in the region of the resonant frequency of the fat component, in particular in the center of the resonance peak. The slices excited by the RF pulse 21 are again illustrated in FIG. 3. The slice 22 is the slice of the water component, the slice 23 is the slice of the fat component. Because of the reversed polarity of the gradient 20 compared to the gradient 13 and a center frequency of the RF pulses 12 and 21 that is at variance with the water resonance, the slices 15 and 22 are shifted with respect to one another. The slices 14 and 23, on the other hand, are at the same height viewed in the slice direction along the axis 16. The slice 23 excited with the second RF pulse 21 provides no signal contribution, as the signal of this slice 23 has previously been saturated. The slice 23 can also be denoted by the reference character 14, as an identical slice is shown in the drawing. However, in practice at least small deviations always arise, two reference characters being justified solely because of the time interval. The signal present in the scan signal therefore originates solely from the slice 22. The fat signal has therefore been suppressed.

The saturation of the slice 15 is a kind of collateral damage, being unnecessary but unavoidable in the context of the method.

The shown saturation of the slice 14 or 23, as the case may be, can also be achieved in a different manner. Instead of using the resonant frequency of the fat protons as the center frequency for the RF pulses 12 and 21, two alternatives can be used.

The first alternative involves taking the resonant frequency of the water protons plus a frequency offset as the center frequency for the first RF pulse 12 or for the second RF pulse 21 and the resonant frequency of the water protons as the center frequency for the other RF pulse. The offset is selected such that the slices 14 and 23 are at the same height, as shown in FIG. 3. Or else the offset is distributed over the two RF pulses 12 and 21 such that the slices 14 and 23 are again at the same height at the end.

Because of the reversal of the gradient 20 compared to the gradient 13, an offset identical in absolute value and sign acts in different directions, the offset therefore having to be reversed in sign when it is added to another RF pulse.

If the offset is uniformly distributed over the two RF pulses 12 and 21 on the basis of the water resonant frequency, the very first alternative is arrived at, in which the resonant frequency of the fat protons is used for the two RF pulses 12 and 21.

In general and without limitation with respect to FIG. 2, preferably on the basis of the resonant frequency of the water protons as center frequency for the RF pulses 12 and 21, an offset frequency corresponding in absolute value terms to twice the difference between the resonant frequencies of the water protons and the fat protons must be distributed over the center frequencies of the two RF pulses 12 and 21. This can be added in full to one of the RF pulses or also distributed as required.

However, it is also possible for this offset to be selected differently. The slices 14 and 23 are then non-identical and a residual signal of the fat component remains. This may be desirable in order to leave this signal as a picture element for orientation. However, this may also result from equipment limitations.

The magnetization of the slice 14 or 23 is only completely saturated if the first RF pulse 12 has a flip angle of 90°. Another flip angle, in particular a smaller flip angle, can also be selected in order to retain a residual fat signal component.

Figure 4:
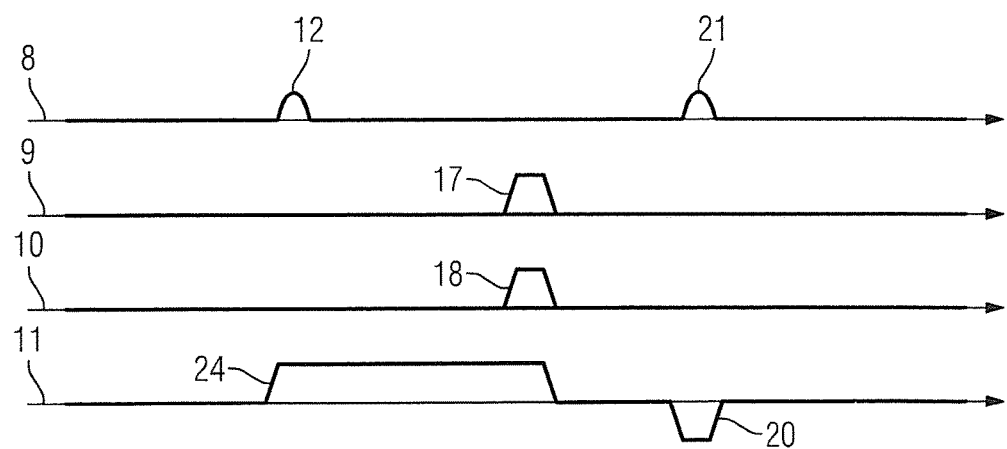
FIG. 4 shows a sequence diagram in a second embodiment of the invention.

FIG. 4 shows a variant of the embodiment of the gradient 19 or of the gradients 13 and 19. Instead of switching the gradient 13 off and the gradient 19 on, the gradient can also be implemented simply as a continuous gradient 24 in the slice direction. To dephase the magnetization excited by the RF pulse 12 it is sufficient to simply not switch the gradient 24 off for a period of time after the end of the RF pulse 12. That is to say, after the end of the RF pulse 12, the function of the gradient 24 changes. It is then no longer used for slice selection but for dephasing the excited spins. Application of the gradients 17 and 18 is not obligatory, in particular the gradients 17, 18 and 24 as well as the gradient 19 do not need to end at the same time and the gradients 17, 18 and 19 do not need to begin at the same time. These are merely preferred embodiments.

The changing of the gradients 13 and 19 to the gradient 24 is the only difference between FIGS. 2 and 4. In particular, in the present application the continuous presence of the gradient 24 is to be understood as applying a first and a second gradient. The reason for this is that the gradient 24, although continuously applied, occasionally experiences a function change and accordingly acts like two different gradients. Claim 1 therefore also includes the embodiment shown in FIG. 4. The gradients 17 and 18 can, but do not need to be applied as additional second gradients. The gradients 17 and 18 cannot be applied during injection of the RF pulse 12.

FIGS. 2 and 4 show only the portion of a sequence in which fat saturation is achieved. Complete sequences will be shown in the following by way of example.

Figure 5:
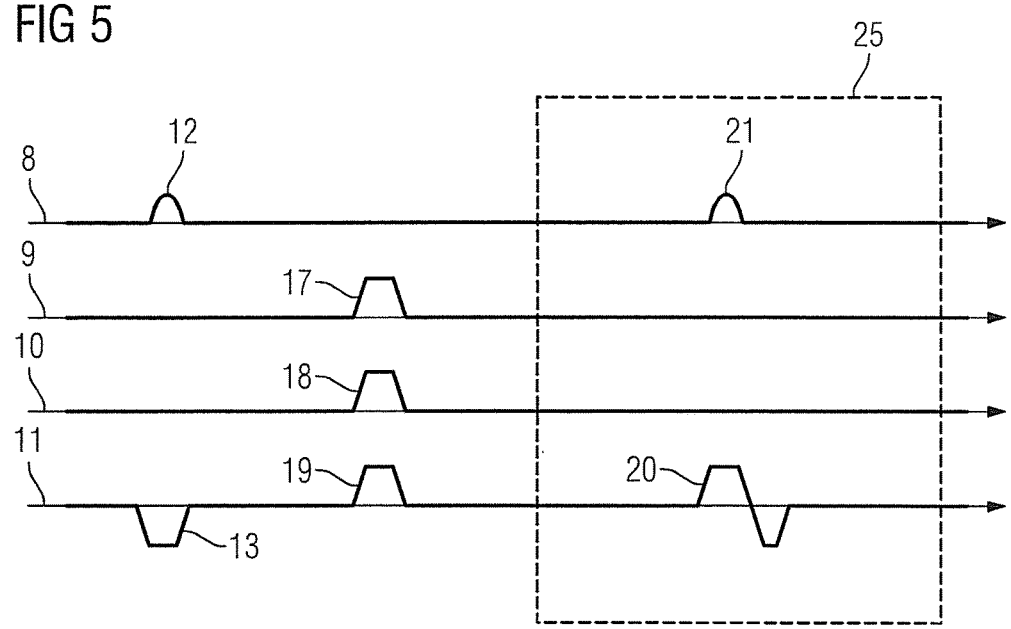
FIG. 5 shows a sequence diagram in a third embodiment of the invention.

FIG. 5 shows a first possibility for incorporating the sequence section shown in FIG. 2, still in general form. After the second gradients 17, 18 and 19, a scan sequence 25 is used to generate a data set, wherein the second RF pulse 21 is the excitation pulse of the scan sequence 25.

This will be illustrated in the subsequent figures using specific embodiments.

Figure 6:
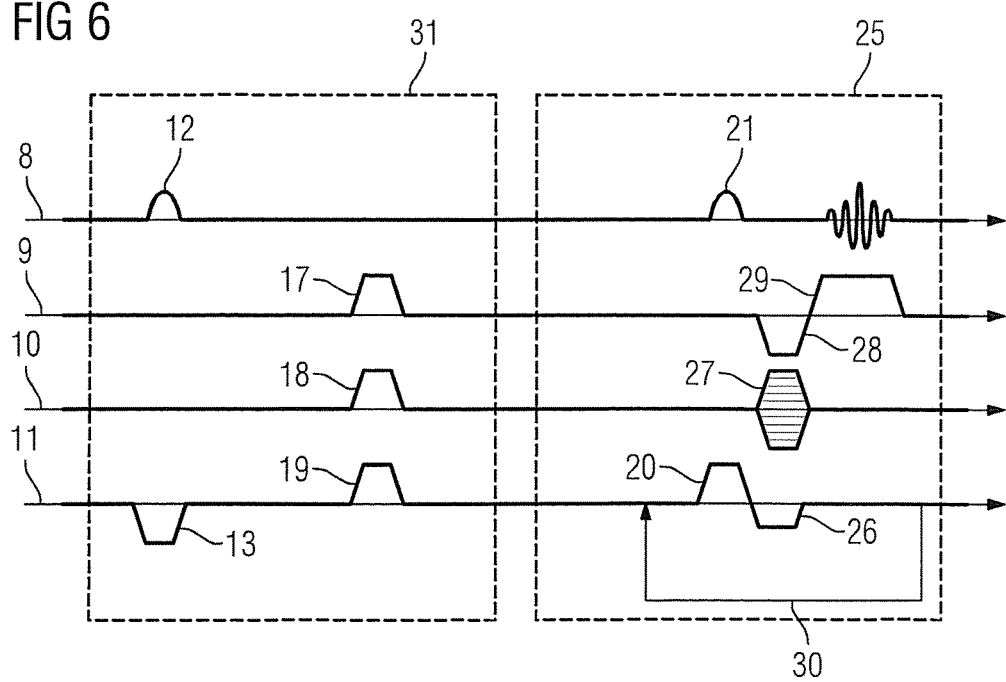
FIG. 6 shows a sequence diagram in a fourth embodiment of the invention.

FIG. 6 shows a sequence diagram in which a FLASH sequence is used as the scan sequence 25. The RF pulse 21 is the excitation pulse having a flip angle of less than 90°, normally in the range 5° to 30°. The third gradient 20 is followed by a gradient 26 for rephasing the spins. The gradients 27 for phase encoding and 28 and 29 in the read direction correspond to the gradients normally used in FLASH imaging, the significance of which does not therefore need to be explained. The arrow 30 indicates that the intervening section is repeated as many times as the number of phase encoding steps provided.

The preparation module 31 is used only once at the start of the experiment.

If the gradients 27, 28 and 29 are omitted, a slice selective, spectroscopic and T1-weighted sequence is obtained.

Figure 7:
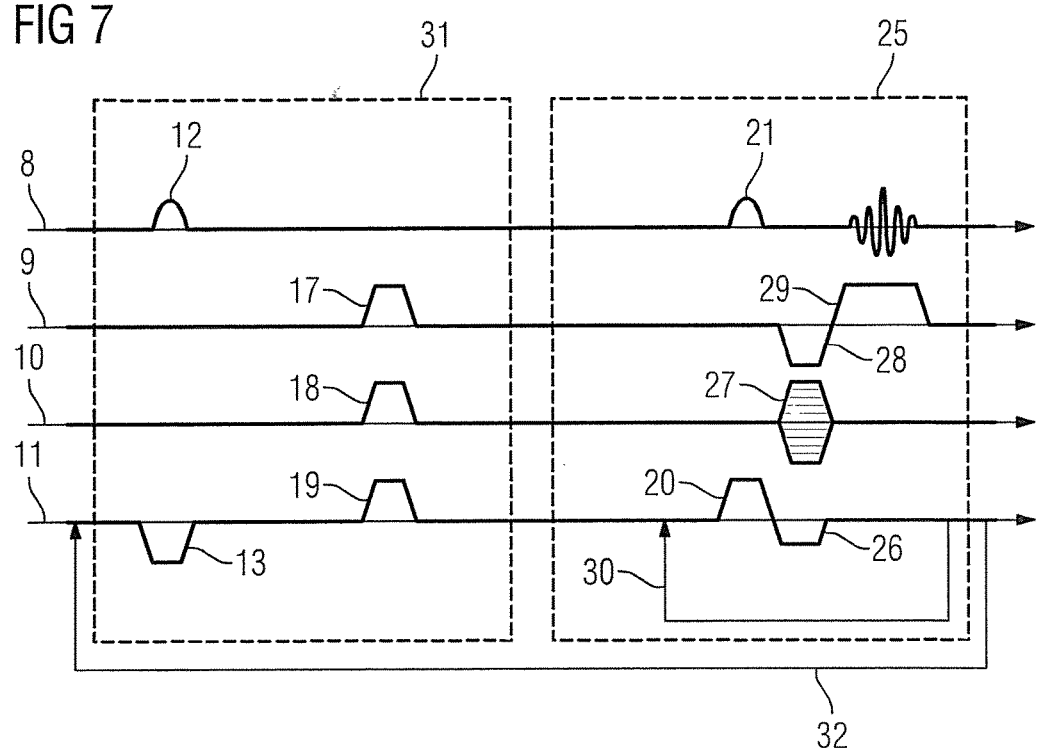
FIG. 7 shows a sequence diagram in a fifth embodiment of the invention.

FIG. 7 shows a sequence according to FIG. 6 in an alternative embodiment. Here the sequence is segmented. The segmentation factor specifies the number of repetitions into which the complete sequence is split up. If this is 8, for example, and the number of phase encoding steps is 128, the number of repetitions of the executed phase encoding steps of the scan frequency 25 is reduced to 16 in the segment. This is then the number of repetitions at the arrow 30. Also present is the arrow 32 which specifies the number of repetitions of the complete sequence, in this case 8. In a segment there is therefore a preparation module 31 and echoes are acquired using 16 different phase encodings. To acquire the 128 echoes, the preparation module 31 is therefore used 8 times. The number of first RF pulses 12 and of second RF pulses 21 can therefore also diverge for all the other scan sequences, but both occur at least once. This consideration also applies analogously to the gradients 13, 17, 18, 19, and 20 or 24 as the case may be.

Figure 8:
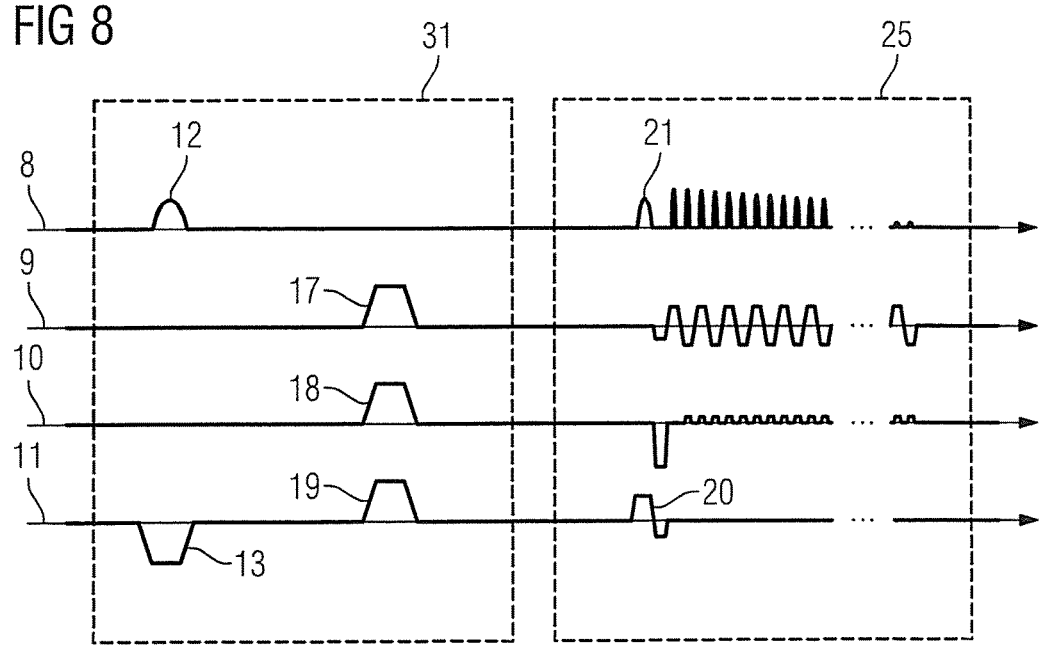
FIG. 8 shows a sequence diagram in a sixth embodiment of the invention.

FIG. 8 shows a sequence diagram in which an EPI is used as the scan sequence. Like FLASH imaging, EPI can also be acquired in one go, so that only one first RF pulse 12 and one second RF pulse 21 are used. The RF pulse 21 is again the excitation pulse of the scan sequence 31. The gradients in the read and phase direction for encoding the k-space lines are known and do not therefore require more detailed explanation. The omission indicates the gradient switches that are not shown.

Figure 9:
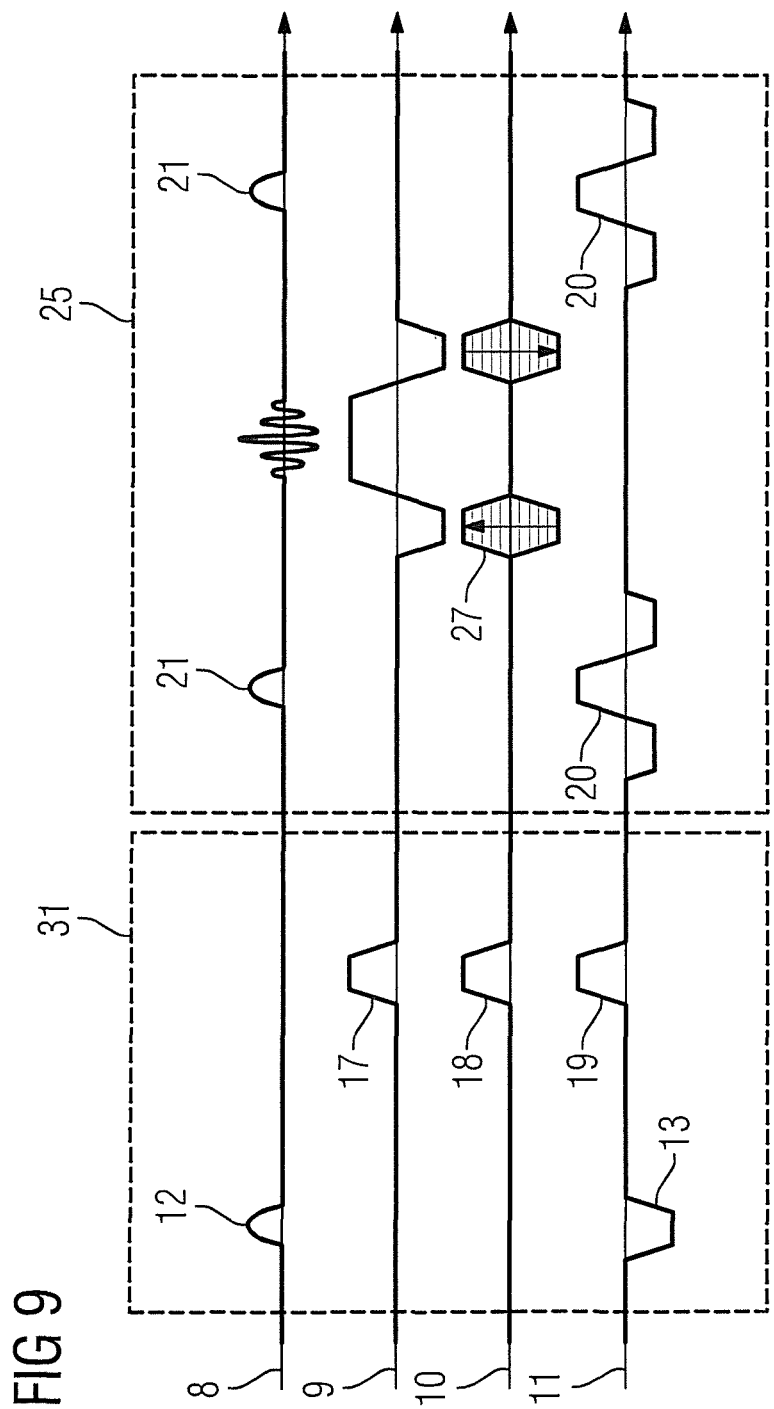
FIG. 9 shows a sequence diagram in a seventh embodiment of the invention.

FIG. 9 forms a sequence diagram having a TrueFISP sequence as the scan sequence 31. As already explained in connection with FIGS. 6 to 8, the sequence according to FIG. 9 can be executed in one go or in a segmented manner.

The use of the preparation module 31, i.e. a preparation module comprising RF pulse and slice encoded gradients and at least one subsequent dephasing gradient, is particularly suitable as a module preceding steady-state sequences. A steady state occurs particularly in the case of gradient echo sequences with short repetition time.

Figure 10:
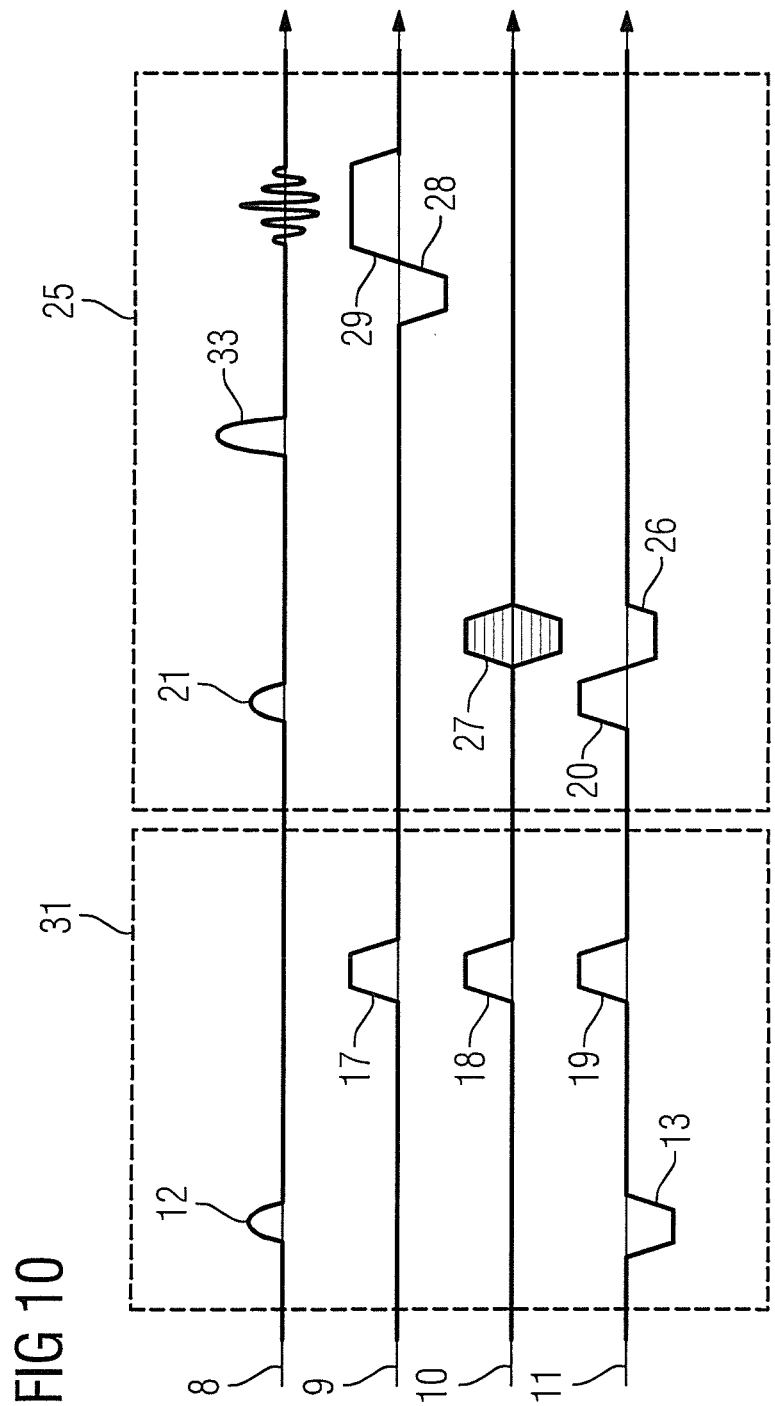
FIG. 10 shows a sequence diagram in an eighth embodiment of the invention.

However, it is also possible to use spin echo or RARE, also known as turbo spin echo or fast spin echo, as the scan sequence 25. A spin echo embodiment is shown in FIG. 10. An RF pulse 21 is followed by another RF pulse 33 which is implemented as a refocusing pulse. To this, a slice gradient not shown in FIG. 10 can also be applied. This must be selected such that the water slice 22 is refocused. Of course, a gradient 24 can also be used here instead of the two gradients 13 and 19. In this embodiment the RF pulse 21 is implemented as a 90° pulse. The center frequency of the refocusing pulse, i.e. of the RF pulse 33, is selected such that it refocuses the slice of the wanted component excited by the RF pulse 21, i.e. the slice 22, for example.

The provision of further refocusing pulses and the modification of the spin echo into a RARE sequence are irrelevant on the basis of FIG. 10.

In the case of a preparation module 31, with particular preference a first RF pulse 12 is used whose center frequency has an offset so that the center frequency is different from the resonant frequency of the wanted component. In particular, the offset can be twice the difference between the resonant frequencies of the wanted and the unwanted component. The wanted component is preferably the water component and the unwanted component the fat component. If the difference between the resonant frequencies is 225 Hz as stated above for protons at 1.5 T, the preferred offset is 450 Hz.

If the offset is only applied to the first RF pulse 12, this has the advantage that only the preparation module 31 must be newly created and then any sequences, in particular steady-state sequences, can be prepended. This enables the number of sequences to be provided on a magnetic resonance scanner to be minimized. In particular, fat suppression can be implemented which can be selected and deselected via a check button. The remainder of the sequence, i.e. the EPI, FLASH or TrueFISP sequence, is already available as a standard module or standard sequence and does not need to be otherwise modified.

Figure 11:
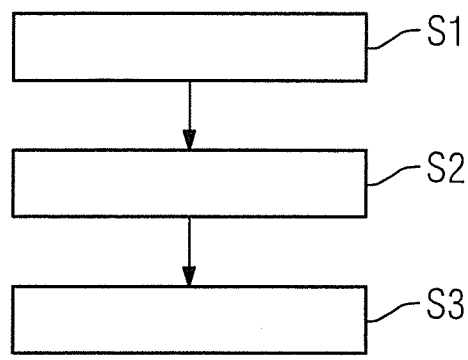
FIG. 11 shows a flowchart of the method according to the invention of the invention.

FIG. 11 shows a general flow chart of the method in the form explained in connection with FIGS. 5 to 10.

In step S1 an RF pulse 12 and a gradient 13 are simultaneously applied. The RF pulse has an offset, in particular an offset of 450 Hz at 1.5 T. In step S2 the thus excited magnetization is then dephased by a gradient 19. As described, a single gradient 24 can also be applied instead of the two gradients 13 and 19.

In step S3 a scan sequence, in particular a standard sequence such as EPI, FLASH, TrueFISP, spin echo or turbo spin, is executed. Here the RF pulse 21 is the excitation pulse of the scan sequence. The gradient 20 applied simultaneously with the RF pulse 21 has a reversed polarity compared to the gradients 13 or 24. Alternatively or additionally, the amplitude of the gradient 20 can be changed compared to the gradient 13 or 24.

It should be pointed out quite generally that the gradient 13 or 24 per se need have neither positive nor negative values. It is only mainly shown with negative values to enable the scan sequence 25 to be represented in the usual manner.

Figure 12:
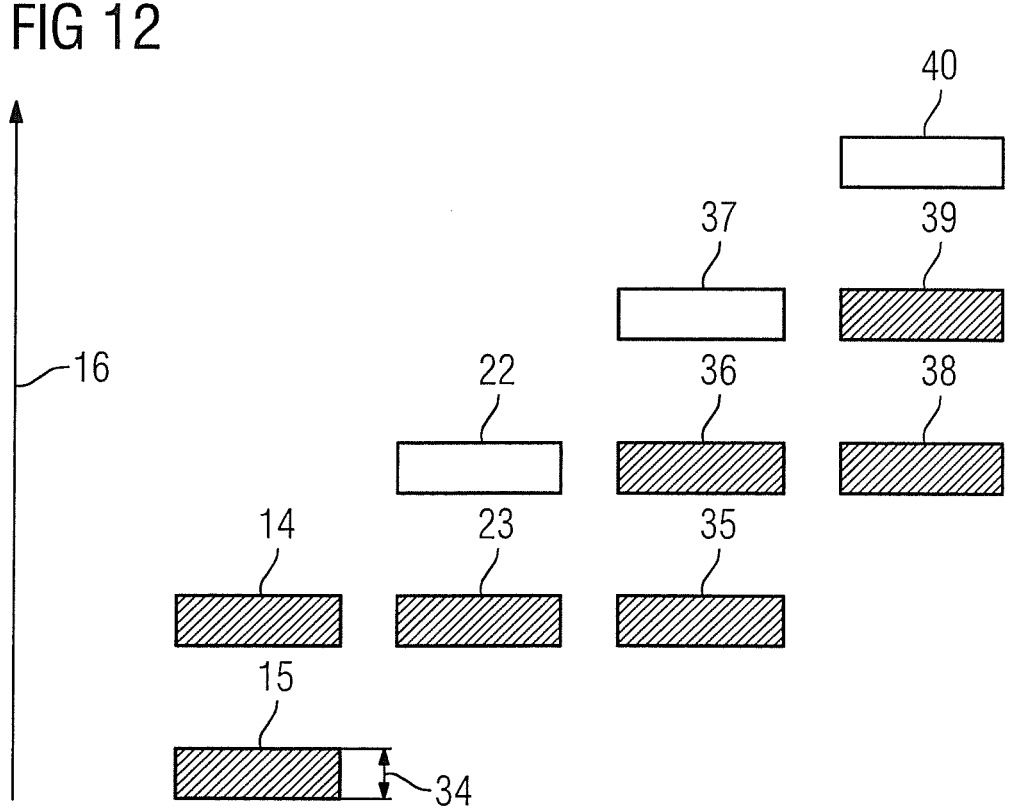
FIG. 12 shows slice positions for a multislice scan.

FIG. 12 shows an embodiment of the method for acquiring a plurality of slices using the example of a sequence, in particular as shown in FIG. 10. Here an adjustment must be performed on the center frequencies in order to enable a plurality of slices to be acquired:

First the first slice 22 or more precisely the first k-space line of the first slice 22 is acquired by proceeding as described in FIG. 10, by way of comparison with FIG. 3. Then an (in absolute value terms) identical shift frequency which shifts the saturated slices and the slice to be acquired in the direction of the slice 22, i.e. upward in FIG. 12, is added to all the RF pulses. The shift can be by any width, but preferably by one or two slice thicknesses. The slice thickness is obviously the height of a slice, here purely by way of example the height 34 of the slice 22. In the case of a shift by one slice thickness, this produces the slices 35, 36 and 37, wherein the saturated and excited (but not yet signal generating) fat slice has been subsumed into the slice 36. The slice 35 is the saturated slice and the slice 37 the read-out slice. The process is continued in this manner so that the read-out slices have not been pre-saturated and always generate the maximum possible signal. Purely by way of example, the slices 38, 39 and 40 are shown accordingly, wherein the slice 39 represents the saturated and read-out (but not signal generating) fat slice, the slice 38 the saturated water slice, and the slice 40 the read-out water slice. The described addition is carried out until all the slices are acquired.

For better differentiation and representation, the water slice to be read out is shown unfilled in each case. The fat slices are also read out, but provide no signal contribution, as they are saturated.

As a k-space line is always acquired for each slice to be read out in the case of spin echo, slice acquisition has to be repeated as many times as there are phase encoding steps provided.

In general, the acquisition of a plurality of slices therefore differs from a single slice in that, to displace all the slices a shift frequency is added to all the RF pulses which shifts the slices of a single slice experiment altogether by a desired distance.

Figure 13:
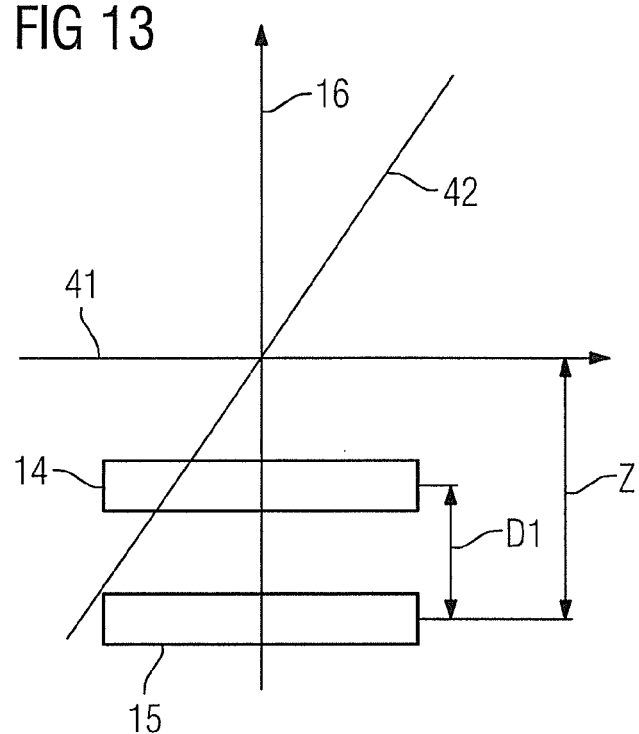
FIG. 13 shows slice preparation in a first section.

Embodiments for selecting scan parameters will be explained with reference to FIGS. 13 and 14.

As described above, the axis 16 gives a measure of the position along the slice gradient Gs, and the axis 41 a measure of the frequency f. The line 42 represents the gradient 13. If the strength of the gradient Gs=G1 and if the chemical shift CS is known, the spatial shift is given by D1=CS/G1. In the case of a chemical shift CS=−3.3 ppm*3T and a gradient strength of G1=2 mT/m, this results in a spatial shift of D1=−5 mm. An additional shift Z of the slices 14 and 15 is produced by adding an offset to the center frequency F of the RF pulse 12: Z=2 pi/gamma*F/G1.

Figure 14:
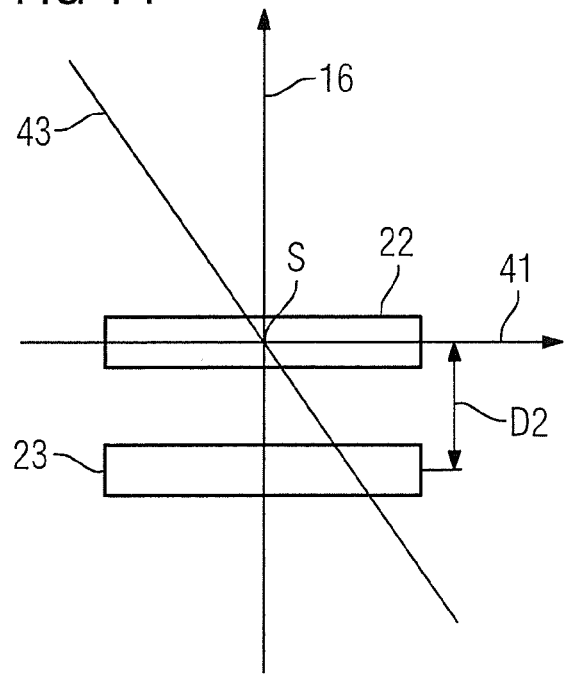
FIG. 14 shows slice preparation in a second section.

In FIG. 14, the line 43 has a reversed slope compared to the line 42, as the polarity of the gradient 19 is of opposite sign to that of the gradient 13. Accordingly, the position of the fat slice 23 and of the water slice 22 is reversed compared to FIG. 13. If the applied gradient G2=−2 mT/m, this results in D2=+5 mm as a new spatial shift. Without the addition of an offset and if the water proton resonant frequency is used as the center frequency F, the slice 22 is in the center S.

In the following, the formulas will be expanded to include the case that the slice SW2 is also outside the center S:

If the first RF pulse 12 has the first center frequency F1=F2+F and the first gradient 13 has the amplitude G1, the position of the water slice can be generalized to $$SW1=2pi/gamma*F1/G1=Z+SW2*G2/G1$$

and the position of the fat slice to $$SF1=(2pi/gamma*F1+CS)/G1=Z+D1+SF2*G2/G1.$$

Similarly, for the second center frequency F2 of the second RF pulse 21 and the third gradient having gradient amplitude G2 we get:

$$SW2=2pi/gamma*F2/G2 \text{ or}$$

$$SF2=(2pi/gamma*F2+CS)/G2=SW2+D2.$$

If the slice thickness is denoted by T, the following conditions arise for complete separation of the water slices 15 and 22 with simultaneous superimposition of the fat slices 14 and 23:

$$|SW2-SW1|>=T \text{ and}$$

$$SF2=SF1.$$

This applies in particular if equation 1

$$F1=(F2+\text{gamma}/2pi*CS)*(G1/G2)-\text{gamma}/2pi*CS \quad (1)$$

i.e. that the fat slices 14 and 23 lie identically, is satisfied as well as condition 2:

$$|1/G1-1/G2|>=T/CS, \quad (2)$$

as a result of which the water slices 15 and 22 do not overlap.

These conditions are independent of the location of the center S, which means that the position of the slice 22 can be placed as required. This is possible using a shift frequency, as described for the multislice experiment. The above described measurement of a plurality of slices is therefore also possible.

With particular preference the following values are selected:

G1=−G2; i.e. only the polarity is changed, with the preferred variables following therefrom:

$$|G2|<=2*CS/T \text{ and}$$

$$F1=-F2-2*\text{gamma}/2pi*CS.$$

If |G2|=2*CS/T is applied, the amplitude of the slice selection gradient is at a maximum and therefore less affected by field inhomogeneities.

If instead of the polarity only the amplitude is changed, the equations 1 and 2 continue to apply. The relationship between the slice selection gradient amplitudes results from condition 2, whereas the necessary center frequency of the first RF pulse results from equation 1. The center frequency of the second RF pulse is generally defined by the defaults of the imaging sequence, e.g. in that the excited slice position of the wanted spin species is predetermined.

With |SW2−SW1|=T protons are only excited to a small extent outside the slice 22, thereby minimizing the effect on adjacent slices.

Setting $$SF2!=SF1$$

results in a residual fat signal being obtained. This is also achievable as described above if the flip angle of the first RF pulse is not equal to 90°.

Selecting |SW2−SW1|<T, the amplitude of the gradient 13 or 24 is increased, thereby reducing the sensitivity to field inhomogeneities. However, this reduces the signal intensity of the water signal.

FIG. 15 shows an embodiment in which the gradient 13 or 24 and/or 20 cannot be set such that the water slice 15 and 22 and the fat slice 14 and 23 are separated. The fat slice 14 and 23 is shown spread out in order to better illustrate the location of the slices. Self-evidently, the slices are of equal width in the examination object.

However, this is not a problem, as the slice 22 is unaffected thereby. It is even possible for the slices 15 and 22 to overlap. In this case the SNR is reduced but a signal is present. Fat suppression therefore basically only requires that the fat slices 14 and 23 essentially coincide apart from wanted deviations.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for generating a magnetic resonance data set, comprising:

operating a magnetic resonance scanner, comprising a radio-frequency (RF) system and a gradient system, in order to apply, from said RF system, a first RF pulse to a subject situated in the scanner comprising two types of nuclei with respectively different resonant frequencies in order to excite said two types of nuclei by giving each of said two types of nuclei a respective magnetization;

simultaneously with applying said first RF pulse, operating said gradient system to apply a first gradient, having a first amplitude and a first polarity, that limits the excitation of a first of said two types of nuclei to a first slice in the subject and that limits excitation of a second of said two types of nuclei to a second slice in the subject;

operating said gradient system to apply at least one second gradient, having a second magnitude and a second polarity, that dephases the magnetization excited by the first RF pulse in both of said first and second slices;

operating the radio-frequency system to apply a second RF pulse in order to also excite said two types of nuclei;

simultaneously with applying said second RF pulse, operating said gradient system to apply a third gradient, having a third amplitude and a third polarity, that limits the excitation of said first of said two types of nuclei by said second RF pulse to a third slice in the subject and that limits the excitation of the second of said two types of nuclei to a fourth slice in the subject, so as to result in said first of said two types of nuclei being excited in a first pair of slices comprising said first slice and said third slice and said second of said two types of nuclei being excited in a second pair of slices comprising said second slice and said fourth slice;

said third gradient satisfying at least one condition selected from the group consisting of said third amplitude being different from said first amplitude and said third polarity being different from said first polarity, said condition causing the slices in one of said first pair or said second pair to completely or partially overlap each other within said one of said first or second pairs, and causing the slices in the other of said first pair or said second pair to not overlap each other within said other of said first or second pairs, and thereby suppressing MR signals from one of said two types of nuclei in said one of said first or second pairs, with MR signals from the other of said two types of nuclei, in said other of said first or second pairs, being unsuppressed; and operating said RF system to read out said unsuppressed MR signals in order to acquire a magnetic resonance data set, and entering said magnetic resonance data set into an electronic memory so as to produce a data file in said electronic memory that is available in electronic form from said electronic memory for further processing.

2. A method as claimed in claim 1 wherein said two types of nuclei are fat protons and water protons, and comprising selecting said first gradient and said third gradient as a function of said first RF pulse and of said second RF pulse to cause the respective slices of the fat protons, respectively excited by said first and second RF pulses, to at least partially overlap in a longitudinal direction of the subject.

3. A method as claimed in claim 2 comprising selecting said first gradient and said third gradient as said function of said first RF pulse and of said second RF pulse to cause the respective slices of the fat protons to have at least one of an identical thickness for an identical position in said longitudinal direction.

4. A method as claimed in claim 1 comprising radiating said first RF pulse with a first center frequency and radiating said second RF pulse with a second center frequency, said first and second center frequencies being different from each other.

5. A method as claimed in claim 1 comprising radiating said first RF pulse with a first center frequency and radiating said second RF pulse with a second center frequency, neither of which corresponds to a resonant frequency of a selected one of said two types of nuclei.

6. A method as claimed in claim 5 wherein said selected one of said nuclei is a water proton.

7. A method as claimed in claim 1 comprising radiating said first RF pulse at a first RF center frequency and radiating said second RF pulse at a second center frequency, each of said first and second center frequencies corresponding to the resonant frequency of a selected one of said two nuclei.

8. A method as claimed in claim 7 wherein said selected one of said two nuclei is fat protons.

9. A method as claimed in claim 1 comprising radiating said first RF pulse with a flip angle that is less than or equal to 90°.

10. A method as claimed in claim 1 comprising radiating said second RF pulse with a flip angle of 90°.

11. A method as claimed in claim 1 comprising radiating said second RF pulse with a flip angle of less than 90°.

12. A method as claimed in claim 1 comprising, after applying said second gradient, operating said scanner according to a scan sequence to read out said signal and generate said data set, with said second RF pulse forming an excitation pulse of said scan sequence.

13. A method as claimed in claim 12 comprising selecting said scan sequence from the group consisting of a FLASH sequence, and EPI sequence, and a TrueFISP sequence.

14. A method as claimed in claim 12 comprising, after applying said second gradient, using a slice selective spectroscopy sequence to read out said signal and generate said data set, with said second RF pulse forming an excitation pulse of said spectroscopy sequence.

15. A method as claimed in claim 1 comprising radiating said first RE pulse as an adiabatic RF pulse.

16. A magnetic resonance apparatus comprising:

a magnetic resonance data acquisition scanner comprising a radio-frequency (RF) system and a gradient system;

a control computer configured to operate said RF system in order to apply a first RF pulse to a subject situated in the scanner comprising two types of nuclei with respectively different resonant frequencies in order to excite said two types of nuclei by giving each of said two types of nuclei a respective magnetization;

said control computer being configured to operate said scanner by, simultaneously with applying said first Rf pulse, operating said gradient system to apply a first gradient, having a first amplitude and a first polarity, that limits the excitation of a first of said two types of nuclei to a first slice in the subject and that limits excitation of a second of said two types of nuclei to a second slice in the subject;

said control computer being configured to operate said scanner by operating said gradient system to apply at least one second gradient, having a second magnitude and a second polarity, that dephases the magnetization excited by the first RE pulse in both of said first and second slices;

said control computer being configured to operate said scanner by operating the radio-frequency system to apply a second RF pulse in order to also excite said two types of nuclei;

said control computer being configured to operate said scanner by simultaneously with applying said second RF pulse, operating said gradient system to apply a third gradient, having a third amplitude and a third polarity, that limits the excitation of said first of said two types of nuclei by said second RF pulse to a third slice in the subject and that limits the excitation of the second of said two types of nuclei to a fourth slice in the subject, so as to result in said first of said two types of nuclei being excited in a first pair of slices comprising said first slice and said third slice and said second of said two types of nuclei being excited in a second pair of slices comprising said second slice and said fourth slice;

said third gradient satisfying at least one condition selected from the group consisting of said third amplitude being different from said first amplitude and said third polarity being different from said first polarity, said condition causing the slices in one of said first pair or said second pair to completely or partially overlap each other within said one of said first or second pairs, and causing the slices in the other of said first pair or said second pair to not overlap each other within said other of said first or second pairs, and thereby suppressing MR signals from one of said two types of nuclei in said one of said first or second pairs, with MR signals from the other of said two types of nuclei, in said other of said first or second pairs, being unsuppressed; and said control computer being configured to operate said scanner by operating said RF system to read out said unsuppressed signals in order to acquire a magnetic resonance data set, and to enter said magnetic resonance data set into an electronic memory so as to produce a data file in said electronic memory that is available in electronic form from said electronic memory for further processing.

* * * * *